(12) United States Patent
Harrison (10) Patent No.: US 7,163,013 B2
(45) Date of Patent: Jan. 16, 2007

(54) APPARATUS FOR THE NASAL OR ORAL DELIVERY OF A MEDICAMENT

(75) Inventor: Ian Harrison, Oxford (GB)

(73) Assignee: Alchemy Healthcare Limited, Oxford (GB)

( * ) Notice: Subject to any disclaimer, the term of this patent is extended or adjusted under 35 U.S.C. 154(b) by 22 days.

(21) Appl. No.: 10/492,013

(22) PCT Filed: Oct. 3, 2002

(86) PCT No.: PCT/GB02/04487

§ 371 (c)(1),
(2), (4) Date: Apr. 5, 2004

(87) PCT Pub. No.: WO03/030973

PCT Pub. Date: Apr. 17, 2003

(65) Prior Publication Data

US 2005/0028813 A1 Feb. 10, 2005

(30) Foreign Application Priority Data

Oct. 5, 2001 (GB) .................................. 0123959.9

(51) Int. Cl.
*A61M 16/00* (2006.01)
(52) U.S. Cl. ..................... 128/203.21; 128/203.15; 128/203.19
(58) Field of Classification Search .......... 128/203.15, 128/203.12, 200.22, 200.23, 203.18, 203.21, 128/203.22, 204.12, 206.11, 207.18; 215/249; 604/410, 905; 206/438; 222/103, 81, 82, 222/88
See application file for complete search history.

(56) References Cited

U.S. PATENT DOCUMENTS

| 3,888,253 A | * | 6/1975 | Watt et al. ............. 128/203.15 |
| 3,906,950 A | * | 9/1975 | Cocozza ................ 128/203.15 |
| 3,908,654 A | * | 9/1975 | Lhoest et al. ................. 604/88 |
| 3,971,377 A | * | 7/1976 | Damani ................. 128/200.17 |
| 4,095,596 A | * | 6/1978 | Grayson ................ 128/203.21 |
| 4,227,522 A | | 10/1980 | Carris |
| 4,338,931 A | * | 7/1982 | Cavazza ................ 128/203.15 |
| 4,353,365 A | | 10/1982 | Hallworth et al. |
| 4,412,573 A | * | 11/1983 | Zdeb .......................... 604/415 |
| 4,995,385 A | * | 2/1991 | Valentini et al. ........ 128/203.21 |
| 5,349,947 A | * | 9/1994 | Newhouse et al. .... 128/203.21 |
| 5,382,236 A | * | 1/1995 | Otto et al. ................... 604/141 |
| 5,398,850 A | * | 3/1995 | Sancoff et al. ........... 222/386.5 |
| 5,715,811 A | * | 2/1998 | Ohki et al. ............. 128/203.21 |
| 5,814,020 A | * | 9/1998 | Gross ......................... 604/141 |

(Continued)

FOREIGN PATENT DOCUMENTS

EP 0129985 B1 9/1988

(Continued)

*Primary Examiner*—Henry Bennett
*Assistant Examiner*—Amadeus Lopez
(74) *Attorney, Agent, or Firm*—Lahive & Cockfield LLP; Anthony A. Laurentano (57) ABSTRACT

An apparatus (1) for the nasal or oral delivery of a medicament, comprises: (a) a sealed flexible container (3) containing the medicament and a gaseous propellant for the medicament; and (b) a delivery device (5), comprising: (i) a main body part (5a) which, at least in use, holds the sealed flexible container (3); and (ii) a compressive part (5b) which, when actuated in use, causes the sealed flexible container (3) to be ruptured and the propellant to expel the medicament from the container, thereby delivering the medicament.

34 Claims, 6 Drawing Sheets

U.S. PATENT DOCUMENTS

| | | | |
|---|---|---|---|
| 5,819,730 A * | 10/1998 | Stone et al. | 128/203.21 |
| 5,823,183 A * | 10/1998 | Casper et al. | 128/203.15 |
| 5,881,719 A * | 3/1999 | Gottenauer et al. | 128/203.15 |
| 5,954,696 A * | 9/1999 | Ryan | 604/141 |
| 6,062,213 A * | 5/2000 | Fuisz et al. | 128/200.21 |
| 6,092,522 A * | 7/2000 | Calvert et al. | 128/203.21 |
| 6,302,101 B1 * | 10/2001 | Py | 128/200.22 |
| 6,810,872 B1 * | 11/2004 | Ohki et al. | 128/203.15 |
| 2003/0101995 A1 * | 6/2003 | Yamashita et al. | 128/203.15 |

FOREIGN PATENT DOCUMENTS

| | | |
|---|---|---|
| GB | 1558985 | 1/1980 |
| WO | WO-83/03976 | 11/1983 |
| WO | WO-94/28956 A1 | 12/1994 |
| WO | WO-99/58180 | 11/1999 |

* cited by examiner

APPARATUS FOR THE NASAL OR ORAL DELIVERY OF A MEDICAMENT

RELATED APPLICATIONS

This application is a 35 U.S.C. 371 national stage filing of International Application No. PCT/GB02/04487, filed 3 Oct. 2002, which claims priority to Great Britain Patent Application No. 0123959.9 filed on 5 Oct. 2001 in Great Britain. The contents of the aforementioned applications are hereby incorporated by reference.

The present invention relates to the nasal or oral delivery of medicaments, and in particular to an apparatus therefor, for example a nasal or oral inhaler.

According to a first aspect, the present invention provides an apparatus for the nasal or oral delivery of a medicament, comprising:
(a) a sealed flexible container containing the medicament and a gaseous propellant for the medicament; and
(b) a delivery device, comprising:
  (i) a main body part which, at least in use, holds the sealed flexible container; and
  (ii) a compressive part which, when actuated in use, causes the sealed flexible container to be ruptured and the propellant to expel the medicament from the containers thereby delivering the medicament.

A second aspect of the invention provides a delivery device for the nasal or oral delivery of a medicament, comprising:
  (i) a main body part arranged to hold, in use, a sealed flexible container containing a medicament and a gaseous propellant for the medicament; and
  (iii) a compressive part arranged to cause, when actuated in use, a sealed flexible container held by the main body part to be ruptured and the propellant to expel the medicament from the container, thereby delivering the medicament.

Preferably the delivery device of the second aspect of the invention comprises the delivery device of the apparatus of the first aspect of the invention. Consequently, once the sealed flexible container containing a medicament and a gaseous propellant is installed in the delivery device according to the second aspect of the invention, the apparatus according to the first aspect of the invention is provided.

The invention has the advantage that it generally provides a simple (both in terms of use and in terms of manufacturability) yet reliable way of delivering a pre-determined dose of a medicament into the nose or mouth of a patient.

Examples of possible therapeutic uses for the invention include: treatments for addictions (e.g. smoking, cocaine or other addictive drugs, obesity, etc.); pharmaceuticals affected by "first pass" metabolism in the gut; female hormones and/or osteoporosis; HIV/AIDS; migraine and/or acute pain; respiratory diseases and/or allergies; vaccines and/or treatment of infectious diseases.

The compressive part of the delivery device preferably comprises a part which is movable with respect to the main body part so as to compress the sealed flexible container. Actuation of the compressive part preferably therefore comprises movement of the compressive part with respect to the main body part such that the sealed flexible container is compressed. Advantageously, such movement of the compressive part may be achieved by depressing, preferably manually, the compressive part with respect to the main body part. Additionally or alternatively, the actuation of the compressive part may comprise the compressive part sliding with respect to the main body part, for example.

In preferred embodiments of the invention, the compressive part is hinged or otherwise rotatably mounted with respect to the main body part of the delivery device. Advantageously, the compressive part may be hinged to the main body part by means of a flexible web (preferably a polymeric web) commonly known as a "living hinge".

The main body part of the delivery device preferably comprises a holding part and a nozzle. The holding part is arranged to retain the sealed flexible container which contains the medicament and the propellant, and the nozzle is arranged to guide the expelled medicament into the nose or mouth (as required) of the patient during use. The holding part preferably includes retaining means to retain the sealed flexible container in place. For example, the holding part may include one or more recesses or the like for receiving and retaining an edge portion of the sealed flexible container.

The compressive part and the main body part of the delivery device preferably include interlockable members such that when the compressive part is depressed, rupturing the sealed flexible container, the compressive part interlocks with the holding part. Preferably such interlocking prevents further depression of the compressive part, for example thereby preventing the compressive part interfering with the delivery of medicament to the patient. Additionally or alternatively, such interlocking of the compressive part with the holding part may prevent a second actuation of the apparatus, thereby making the apparatus a single use apparatus. In this way, the patient is prevented from attempting to re-use the apparatus once the medicament has been delivered, thereby preventing the patient from inadvertently re-using the apparatus and believing that he has received a dose of medicament when in fact he has not. Advantageously, the apparatus may include a visible indication of when the apparatus has been actuated—for example a suitably coloured portion on the compressive part and/or the holding part—which is visible only once the apparatus has been actuated.

The sealed flexible container preferably is installed in the delivery device prior to its supply to the patient, and this is preferably achieved by the delivery device being openable by means of the above mentioned hinge or other rotatable mounting of the compressive part with the holding part. Once the sealed flexible container has been installed in the delivery device, the delivery device preferably is closed around the container. Advantageously, the closing of the delivery device may be achieved by means of interlockable members of the main body part and the compressive part; preferably these are the same interlockable members which interlock when the apparatus is actuated. Most preferably, the main body part and the compressive part of the delivery device include interlockable members which are arranged to undergo a two-stage interlocking action. The first interlocking action preferably closes the delivery device, for example around the sealed flexible container installed in the device. The second interlocking action preferably occurs upon actuation of the apparatus. As mentioned above, once the second interlocking action has occurred, an indicator (e.g. a coloured indicator) preferably is visible, indicating that the apparatus has been actuated and cannot (or should not) be re-actuated.

Preferably once the apparatus has been actuated and the medicament has been delivered to the patient, the device is closed in such a way that it cannot easily be reopened, thereby substantially preventing the removal of the flexible container. The apparatus may be closed by means of the above-mentioned interlockable members of the compressive part and the holding part of the delivery device, for example.

The delivery device is preferably formed from a polymer material, for example a polyolefin (e.g. polyethylene and/or polypropylene) or a polyacrylate (e.g. polymethylmethacrylate). The delivery device is preferably moulded, for example injection moulded or blow moulded. The device is preferably moulded as a single integral part.

The sealed flexible container is preferably formed from metal foil and/or flexible polymeric sheet material. Most preferably the container is formed from a laminate of one or more layers of metal foil and polymeric sheet material, e.g. a laminate of aluminium foil and polyethylene sheet. The container is preferably heat sealed. As an alternative to a laminated container it may be made from a single hinged moulded part or two separate moulded parts to be sealed at the filling stage, for example. Preferably the container provides a barrier to air and micro-organisms and prevents leakage of the medicament, any excipients or propellant.

Advantageously the flexible container may include a frangible portion which is designed to rupture when the container (containing the gaseous propellant and the medicament) is compressed, in use, by the compressive part. The frangible portion preferably takes the form of one or more lines of weakness along which the container is designed to break when so compressed; such lines of weakness may have the form of an arc or a star shape, for example. The frangible portion is arranged such that when the sealed container is installed in the delivery device it is located adjacent to the nozzle of the device, thereby facilitating delivery of the medicament to the patient.

An alternative (or an addition) to the weakness lines on the leading edge of the medicament pouch (i.e. the flexible container) is a modification to the body of the device. A rear-facing protrusion adjacent to the noble (e.g. an annular protrusion) may be required, e.g. to assist in the release of medicament from some types of laminates or plastics used for forming the pouch. The actuation pressure from the user's thumb on the top of the device will depress the top surface of the pouch and drive it forward onto the annular protrusion. This will lead to the pouch bursting at this point to facilitate the release of medicament through the front of the pouch and onwards into the delivery "tunnel" to the nasal cavity. The annular protrusion may also act as a sealing feature, preventing loss of contents and pressure, for example.

For the atomisation of some liquids to be delivered it may be necessary to include within (or adjacent to) the "tunnel" of the nozzle a baffle, sieve, mesh insert, or other atomising means.

The gaseous propellant contained in the sealed flexible container may be at a pressure above atmospheric pressure (i.e. pressurized) prior to the compression of the flexible container by the compressive part of the delivery device (i.e. the gaseous propellant may be pressurized as supplied in the flexible container). Alternatively, the gaseous propellant may be substantially at (or even below) atmospheric pressure as supplied, and pressurized only upon compression of the flexible container by the compressive part of the device.

Examples of suitable propellants contained within the container include: air, oxygen, nitrogen, argon, or substantially any non-CFC propellant suitable for human inhalation. The medicament may be in powder and/or liquid and/or vaporous and/or gaseous form; for example it may be inhaled in the form of a spray and/or a powder.

The invention will now be described, by way of example with reference to the accompanying drawings, of which:

FIG. 3 (views (a) to (c)) shows, schematically, the assembly and use of the apparatus of FIGS. 1 and 2;

FIG. 4 (views (a) to (d)) shows, schematically, a further embodiment of the apparatus according to the invention;

FIG. 5 (views (a) and (b)) shows another embodiment of the apparatus prior to delivery of its medicament; and FIG. 6 (views (a) and (b)) shows the embodiment of the apparatus shown in FIG. 5, during delivery of the medicament.

Figure 1:
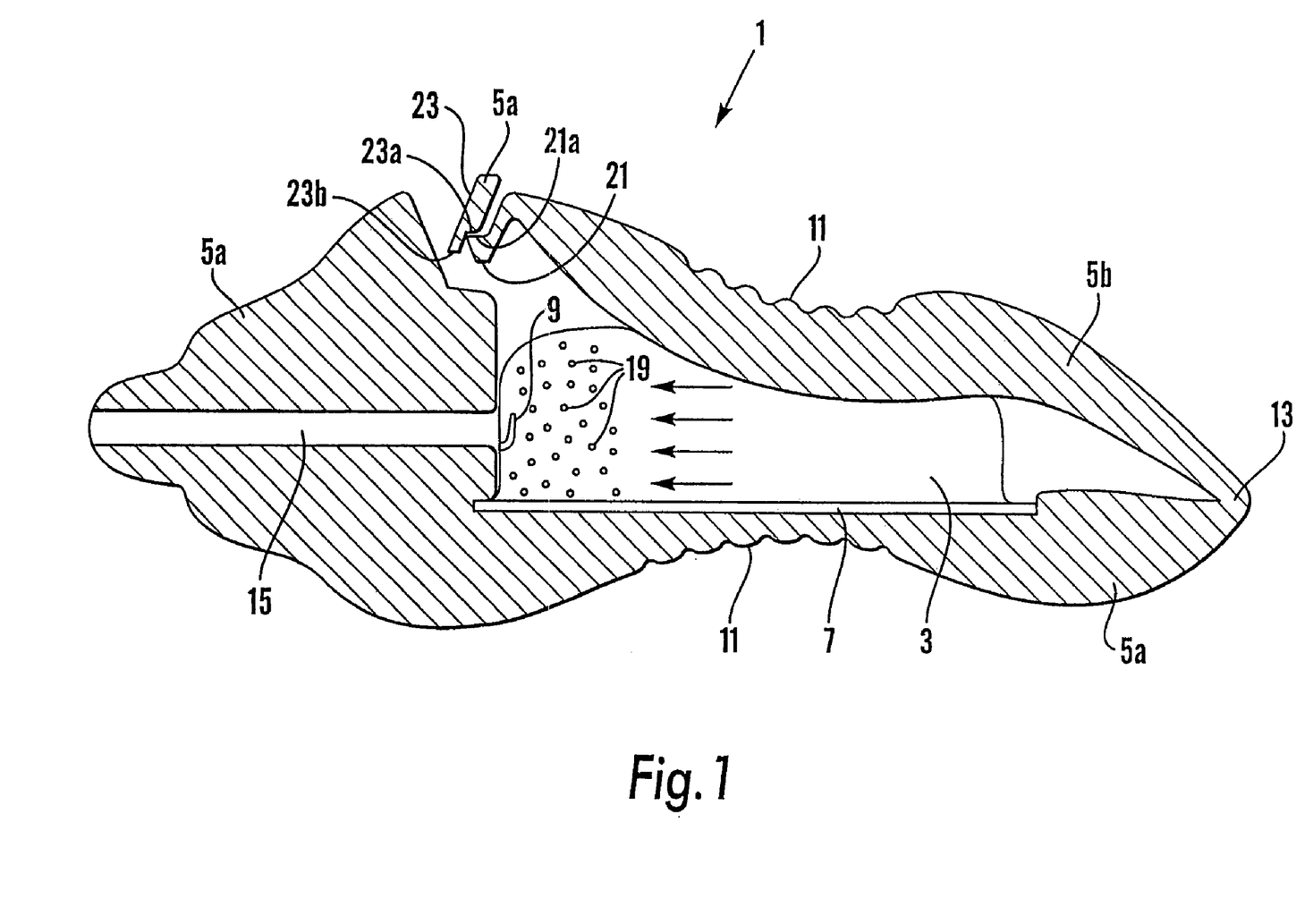
FIG. 1 shows an embodiment of the apparatus according to the invention, in cross-section, prior to delivery of its medicament.

FIG. 1 shows an apparatus 1 for the nasal or oral delivery of a medicament, comprising a sealed flexible container 3 containing the medicament and a gaseous propellant for the medicament, and a delivery device 5. The delivery device 5, which is moulded from polymer material, comprises a main body part 5a which, at least in use, holds the sealed flexible container 3, and a compressive part 5b which, when actuated in use, causes the sealed flexible container 3 to be ruptured and the propellant to expel the medicament from the container, thereby delivering the medicament. The sealed flexible container 3 is a heat sealed laminate of aluminium foil and polyethylene, heat sealed flat-edges of which are retained in a recess 7 of the main body part 5a of the delivery device 5. The container contains pressurized propellant gas and a medicament in liquid or powder form. The container includes a frangible portion 9 in the form of a line of weakness which is designed to rupture when the container is compressed sufficiently.

The delivery device 5 includes a pair of opposed finger grips 11, one on the compressive part 5b and the other on the main body part 5a. The delivery device also includes an integrally moulded flexible web 13 at a rear end of the device which acts as a "living hinge", and at the opposite, front, end of the device there is a nozzle 15 by which the medicament is delivered to a patient. (The nozzle 15 as shown is for nasal use; it would generally be modified for oral inhalation.) In use, the patent grips the apparatus between the thumb and one or more fingers of the same hand and squeezes the compressive part 5b and the main body part 5a of the delivery device together (i.e. the compressive part is depressed with respect to the main body part). This actuation of the device compresses the sealed flexible container 3 between the compressive part 5b and the main body part 5a, thereby pressurizing the propellant gas within the container. The pressure of the propellant gas upon the frangible portion 9 of the container causes the frangible portion to rupture, as indicated by reference numeral 17 in FIG. 2, thereby releasing the propellant gas and the medicament 19 contained in the container, both of which are expelled from the apparatus via the nozzle 15 (as indicated by the arrow in FIG. 2). In this way the medicament is delivered to the nose or throat of the patient.

A front portion 21 of the compressive part 5b and an adjacent portion 23 of the main body part 5a comprise interlockable portions. The interlockable portions 21 and 23 are arranged to undergo a two-stage interlocking action. The first interlocking stage occurs when the delivery device 5 is closed around the sealed flexible container 3, once the container is installed in the device in the assembly plant. The apparatus 1 therefore is supplied to the end-user with the delivery device 5 closed by means of the interlockable portions 21 and 23 in their first interlocking stage—as shown in FIG. 1, i.e. with portion 21 of the compressive part interlocked with surface 23a of portion 23. When the compressive part 5b is actuated in use, by being depressed with respect to the main body part 5a, the interlocking portions 21 and 23 undergo their second interlocking stage—as shown in FIG. 2, i.e. with portion 21 of the compressive part interlocked with surface 23b of portion 23.

Upper facing surface 21a of portion 21 is provided with a coloured, indicator mark (e.g. a red indicator strip) which is not visible in the first interlocking stage but is visible once the apparatus has been used, i.e. in the second interlocking stage. In this way the patient is provided with a visible means of indication that the apparatus has been used and cannot be used again. A shoulder 25 on the main body part prevents over depression of the compressive part 5b (which could otherwise block the nozzle 15 hindering the delivery of the medicament).

Figure 2:
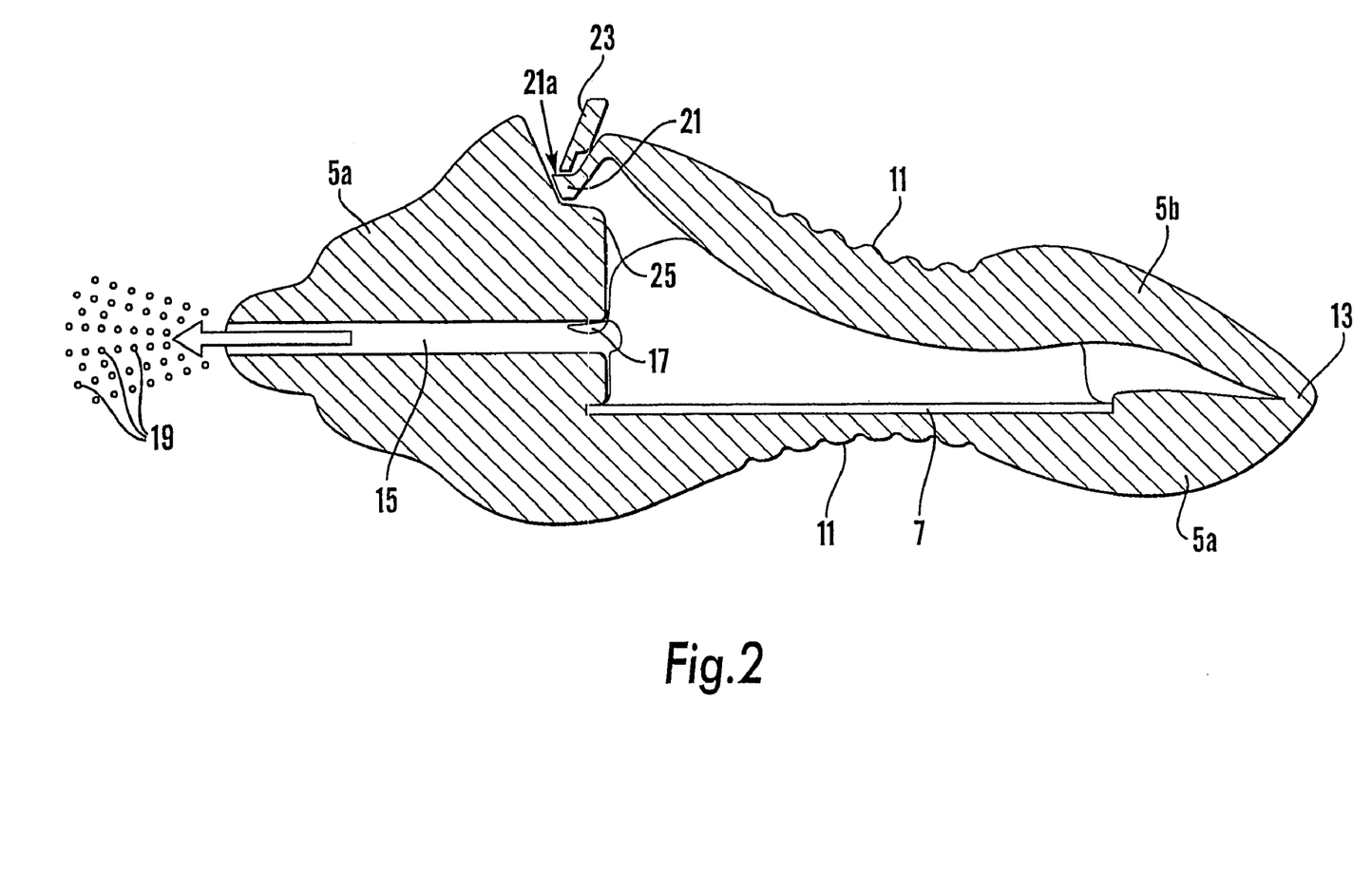
FIG. 2 shows, in cross-section, the embodiment of FIG. 1 during delivery of the medicament.
Figure 3A:
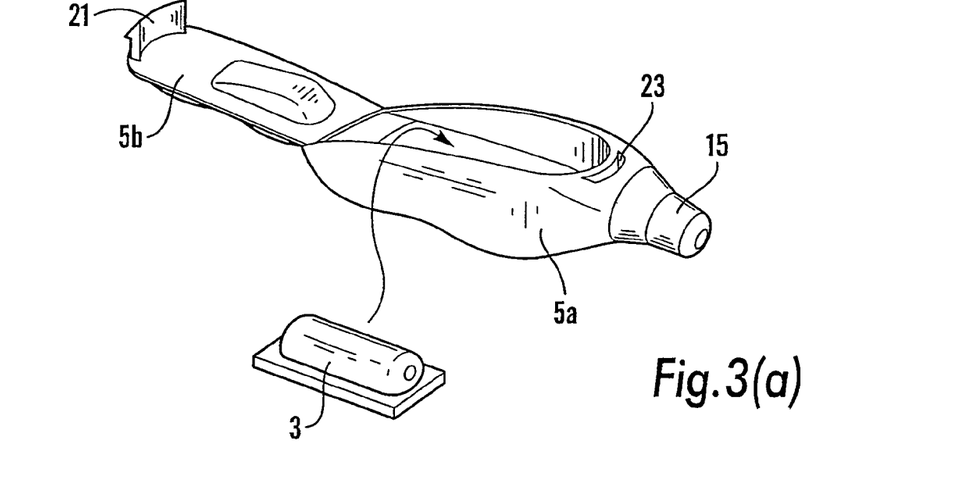
Figure 3B:
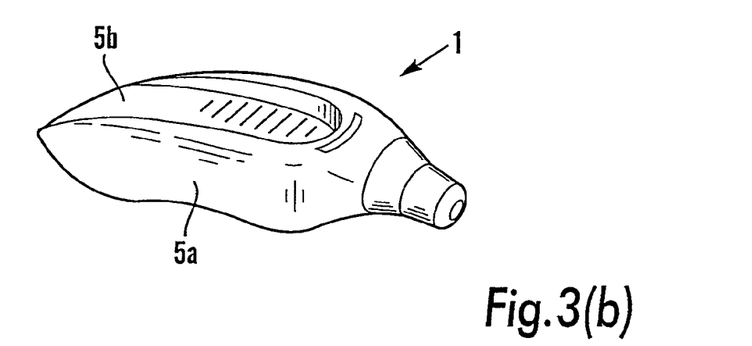
Figure 3C:
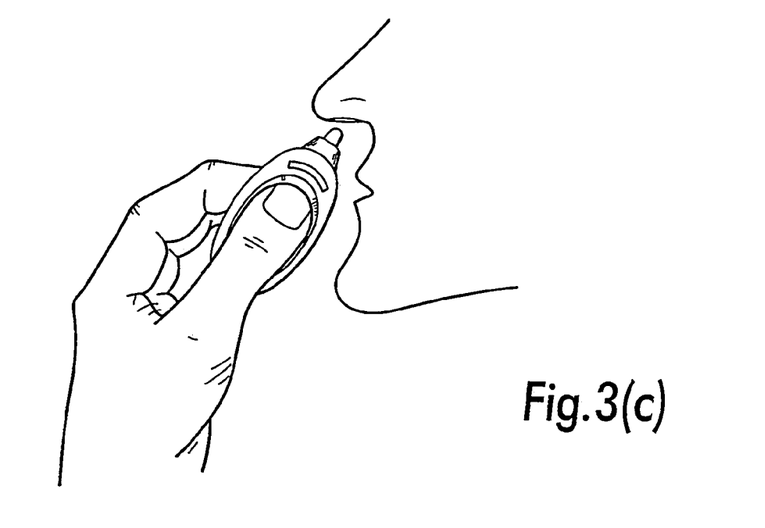

FIG. 3(a) is a schematic view illustrating the installation of the sealed flexible container 3 in the form of a "blister pack" in the delivery device 5 of the apparatus shown in FIGS. 1 and 2. FIG. 3(b) shows the apparatus with the container 3 installed; the interlockable-portions 21 and 23 have interlocked in the first of their two-stage interlocking action. FIG. 3(c) shows a patient using the apparatus to deliver a medicament nasally. It can be seen from FIGS. 3(a) and 3(b) that in this embodiment of the invention the compressive part 5b is recessed within the main body part 5a of the apparatus. This diminishes the possibility of inadvertent actuation during packaging or transportation, for example.

FIG. 4 shows another embodiment of the apparatus 1 according to the invention, in which the compressive part 5b is larger than that of the embodiment shown in the preceding figures. FIG. 4(a) is a side view showing the main body part 5a and the compressive part 5b of the delivery device fully opened to allow the insertion of a sealed flexible container 3 (not shown) containing the medicament and propellant, into the apparatus 1. The main body part 5a includes the nozzle 15 for delivering the medicament. A recess 7 for retaining a heat-sealed flat edge of the flexible container is shown, as are interlockable portions 21 and 23 of the delivery device, portion 23 being an aperture in which the projection 21 is receivable. The delivery device is opened by means of a flexible polymeric web 13 which functions as a living hinge.

Figure 4A:
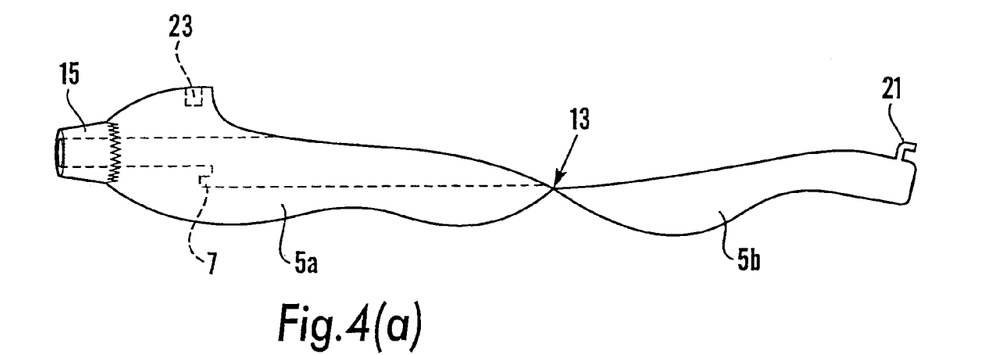
Figure 4B:
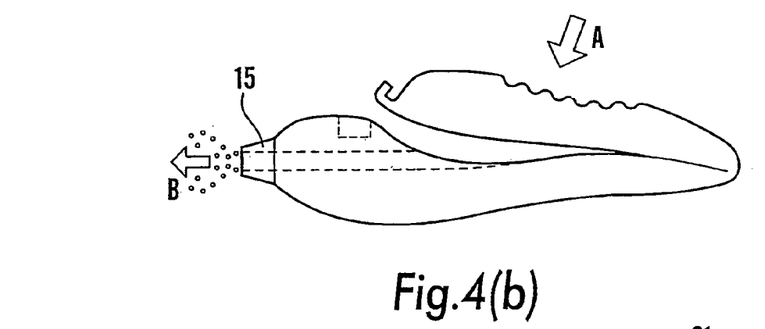

FIG. 4(b) shows the delivery device being actuated by the compressive part 5b being depressed with respect to the main body part 5a, as indicated by arrow A. In this embodiment of the invention, the delivery device is partially open prior to actuation (i.e. the two stage interlocking action described above is not present in this embodiment). The depression of the compressive part 5b with respect to the main body part 5a compresses the sealed flexible container (not shown) which has been inserted into the delivery device. The compression of the sealed flexible container causes the container to rupture, and causes the propellant in the container to expel the medicament from the container, thereby delivering the medicament to the patient via the nozzle 15, as indicated by arrow B.

Figure 4C:
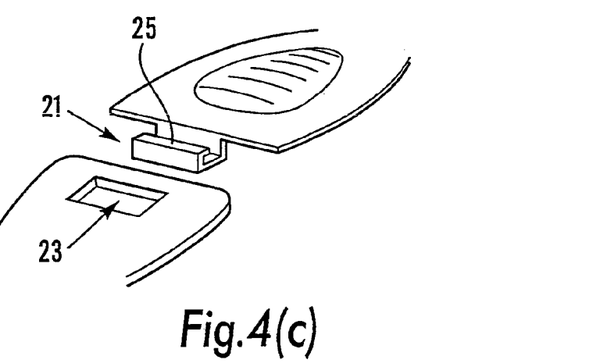

FIG. 4(c) shows a detail of the interlockable portions 21 and 23 prior to their interlocking during actuation of the apparatus 1 as shown in FIG. 3(b). The portion 21 includes a coloured indication mark 25 (e.g. a red mark) which is visible through the aperture 23 when the compressive part has been fully actuated and portion 21 has interlocked with aperture 23. This provides a visible indication that the apparatus has been used and cannot be re-used.

Figure 4D:
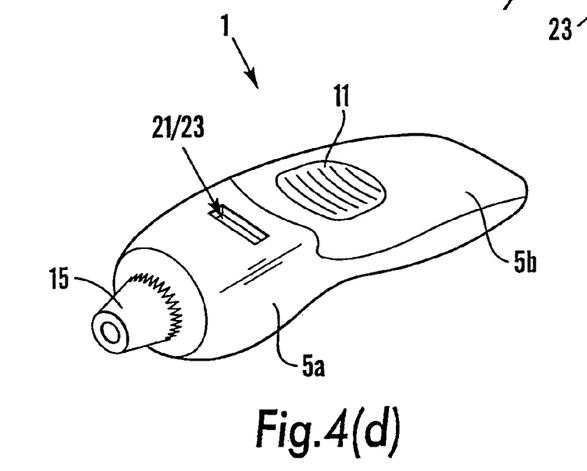

FIG. 4(d) shows the apparatus 1 subsequent to its actuation as shown in FIGS. 4(b) and (c). The apparatus is fully closed, i.e. the main body part 5a and the compressive part 5b of the delivery device are interlocked with each other by means of portions 21 and 23. The finger grip 11 of the compressive part is visible, but the finger grip of the main body part is depressed.

Figure 5A:
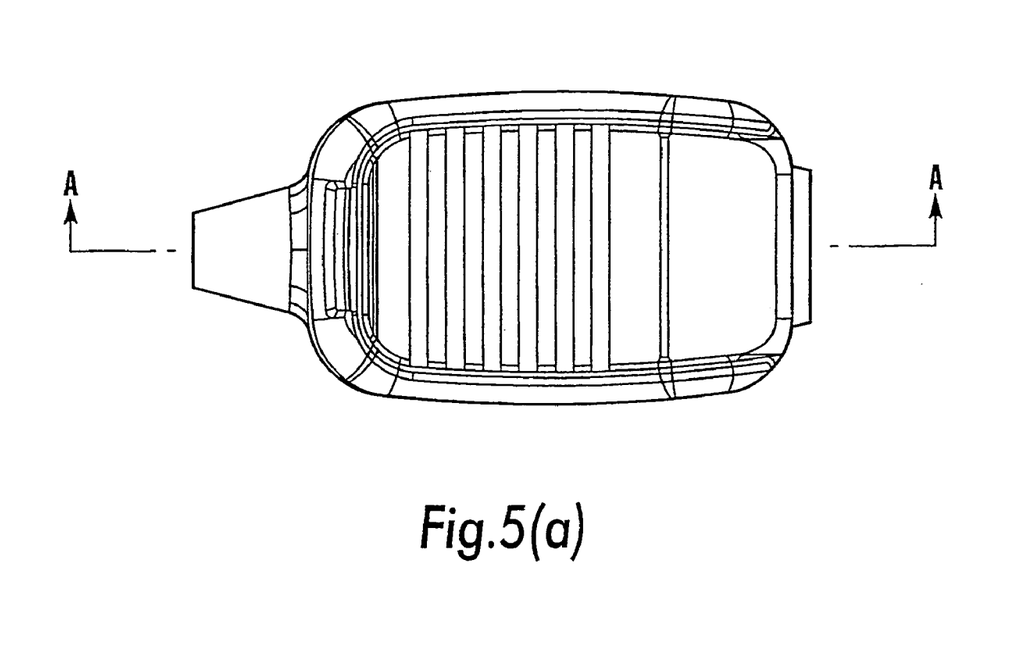
Figure 5B:
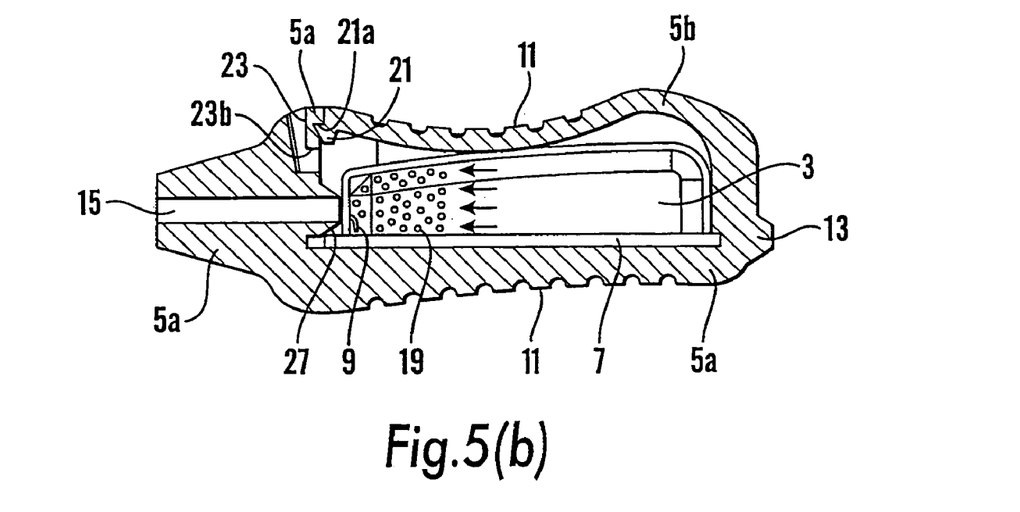
Figure 6A:
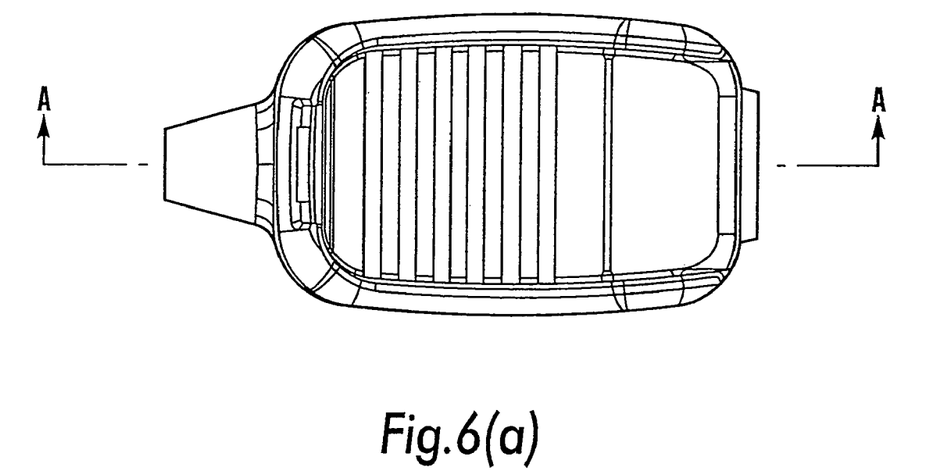
Figure 6B:
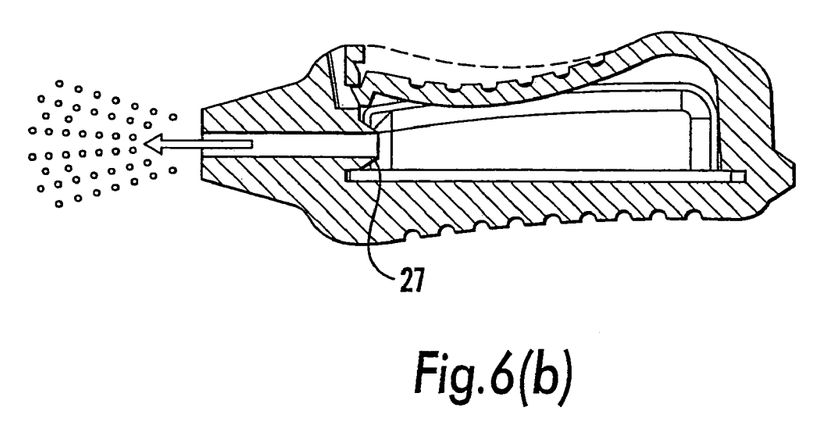

FIG. 5(a) shows a plan view, and FIG. 5(b) shows a cross-sectional side view, of another embodiment of the apparatus according to the invention prior to the delivery of its medicament. This embodiment is similar to the previously described embodiments, with like features indicated by the same reference numerals. However, this embodiment includes a rear-facing protrusion 27 in the form of an annular protrusion surrounding the inwardmost entry to the nozzle of the delivery device. This protrusion assists in the rupture of the flexible container and the consequent release of the medicament and the gaseous propellant. The protrusion also helps to provide a degree of sealing between the ruptured container and the nozzle, and assists the guidance of the medicament and propellant into and through the nozzle. FIG. 6 (views (a) and (b)) shows this embodiment of the invention during delivery of the medicament.

The invention claimed is:

1. An apparatus for the nasal or oral delivery of a medicament to a patient, comprising:
    (a) a sealed flexible container including the medicament and a gaseous propellant for the medicament; and
    (b) a delivery device, including:
        (i) a main body part which, at least in use, holds the sealed flexible container, the main body part including a nozzle by which the medicament is delivered to the patient; and
        (ii) a compressive part which, when actuated in use, compresses the sealed flexible container, thereby pressurizing the gaseous propellant within the container, which pressurization of the gaseous propellant causes to sealed flexible container to be ruptured and the propellant to expel the medicament from the apparatus, thereby delivering the medicament to the patient;
    wherein the main body part includes a protrusion adjacent to the nozzle, to assist the rupturing of the sealed flexible container, the protrusion being arranged such that the compression of the sealed flexible container by the compressive part causes the sealed flexible container to be driven against the protrusion and thereby to be ruptured where it meets the protrusion.

2. The apparatus according to claim 1, wherein the sealed flexible container is formed from one of a metal foil and a polymeric sheet material.

3. The apparatus according to claim 2, wherein the sealed flexible container comprises a laminated structure formed from a metal foil laminated to a polymeric sheet material.

4. The apparatus according to claim 1, wherein the sealed flexible container is molded and comprises one or more parts.

5. The apparatus according to claim 1, wherein the sealed flexible container comprises a frangible portion adapted to rupture when the compressive part of the delivery device is actuated in use.

6. The apparatus according to claim 1, wherein the propellant included in the sealed flexible container comprises one or more of air, oxygen, nitrogen, argon, and substantially any non-CFC propellant suitable for human inhalation.

7. The apparatus according to claim 1, wherein the medicament is in one or more of a powder form, a liquid form, a vapor form, and a gaseous form.

8. The apparatus according to claim 1, wherein each of the compressive part and the main body part include an interlockable member, such that when the compressive part is actuated the compressive part interlocks with the main body part.

9. The apparatus according to claim 8, wherein the interlockable members are arranged to undergo a two-stage interlocking action including a first stage and a second stage, wherein the first stage includes closure of the delivery device to hold the sealed flexible container, and wherein the second stage occurs open actuation of the compressive part.

10. The apparatus according to claim 1, wherein the compressive part comprises a part which is movable with respect to the main body part so as to compress the sealed flexible container, and actuation of the compressive part includes such movement.

11. The apparatus according to claim 1, wherein actuation of the compressive part is arranged to be carried out by manual depression of the compressive part with respect to the main body part.

12. The apparatus according to claim 1, wherein the compressive part is one of hinged and rotatably mounted with respect to the main body part.

13. The apparatus according to claim 12, wherein the compressive part is hinged to the main body part by a flexible web.

14. The apparatus according to claim 1, further comprising atomizing means, disposed in or adjacent to the nozzle, to atomize a liquid medicament.

15. The apparatus according to claim 1, further comprising a visible indicator for indicating when the apparatus has been activated.

16. The apparatus according to claim 15, wherein the visible indicator comprises a colored portion disposed on one of the compressive part and the main body part.

17. The apparatus according to claim 1, wherein the protrusion is an annular protrusion surrounding any entry to the nozzle.

18. A delivery device for the nasal or oral delivery of a medicament, comprising:
(i) a main body part arranged to hold, in use, a sealed flexible container containing a medicament and a gaseous propellant for the medicament the main body part including a nozzle by which the medicament is delivered to the patient; and
(ii) a compressive part arranged to cause, when actuated in use, a sealed flexible container held by the main body part to be ruptured and the propellant to expel the medicament from the container, thereby delivering the medicament, wherein each of the compressive part and the main body part include an interlockable member by which the compressive part may interlock with the main body part, wherein the interlockable members are arranged to undergo a two-stage interlocking action including a first stage and a second stage, wherein the first stage includes closure of the delivery device to hold the sealed flexible container, and wherein the second stage occurs upon actuation of the compressive part; and wherein the main body part includes a protrusion adjacent to the nozzle, to assist the rupturing of the sealed flexible container, the protrusion being arranged such that the compression of the sealed flexible container by the compressive part causes the sealed flexible container to be driven against the protrusion and thereby to be ruptured where it meets the protrusion.

19. The device according to claim 18, wherein the compressive part comprises a part which is movable with respect to the main body part so as to compress the sealed flexible container, and actuation of the compressive part comprises such movement.

20. The or device according to claim 18, wherein actuation of the compressive part is arranged to be carried out by manual depression of the compressive part with respect to the main bodypart.

21. The device according to claim 18, wherein the compressive part is one of hinged and rotatably mounted with respect to the main body part.

22. The device according to claim 21, wherein the compressive part is hinged to the main body part by a flexible web.

23. The device according to claim 18, in which the main body part comprises a nozzle by which the medicament is delivered, in use.

24. The device according to claim 23, wherein the main body part comprises a protrusion, adjacent to the nozzle, to assist the rupture of the flexible container.

25. The device according to claim 23, further comprising atomizing means, disposed in or adjacent to the nozzle, to atomize a liquid medicament.

26. The device according to claim 18, wherein the interlocking of the interlockable members prevents re-actuation of the compressive part.

27. The device according to claim 18, wherein, when the compressive part has been actuated, the compressive part interlocks with the main body part such that further depression of the compressive part is substantially prevented.

28. The device according to claim 18 further comprising a visible indicator for indicating when the device has been actuated, which is visible only once the apparatus has been actuated.

29. The device according to claim 28, wherein to visible indicator comprises a colored portion disposed on one of the compressive part and the main body part.

30. The device according to claim 18, wherein the delivery device is formed from a polymer material.

31. The device according to claim 30, in which the delivery device is molded as a single integral part.

32. The device according to claim 18, wherein the gaseous propellant contained in the sealed flexible container is in a pressurized state prior to actuation of the compressive part.

33. The device according to claim 18, wherein the gaseous propellant is pressurized only upon actuation of the compressive part.

34. The apparatus according to claim 18, wherein the protrusion is an annular protrusion surrounding an entry to the nozzle.

* * * * *